(12) United States Patent
Steinlein et al.

(10) Patent No.: US 6,242,656 B1
(45) Date of Patent: Jun. 5, 2001

(54) METHOD FOR PRODUCING A DINITRONAPHTHALENE-ISOMER MIXTURE HAVING A HIGH 1,5-DINITRONAPHTHALENE PROPORTION

(75) Inventors: Christian Steinlein, Ratingen; Gerhard Wegener, Mettmann, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/486,686

(22) PCT Filed: Aug. 26, 1998

(86) PCT No.: PCT/EP98/05408

§ 371 Date: Mar. 1, 2000

§ 102(e) Date: Mar. 1, 2000

(87) PCT Pub. No.: WO99/12887

PCT Pub. Date: Mar. 18, 1999

(30) Foreign Application Priority Data

Sep. 8, 1997 (DE) ............................................. 197 39 202

(51) Int. Cl.⁷ ................................................. C07C 205/00
(52) U.S. Cl. .............................................................. 568/930
(58) Field of Search ............................................. 568/930

(56) References Cited

U.S. PATENT DOCUMENTS 4,053,526 * 10/1977 Blank et al. .......................... 260/645

FOREIGN PATENT DOCUMENTS

| 1150965 | 7/1963 | (DE) . |
| 2453529 | 5/1976 | (DE) . |
| 1248426 * | 1/1959 | (FR) . |
| 94/19310 | 9/1994 | (WO) . |

OTHER PUBLICATIONS

Hauben–Weyl, Methoden der Organischen Chemie, (month unavailable) 1971, vol. 10, pp. 492–495, W. Seidenfaden u. D. Pawellek, "Aromatische Nitro–Verbindungen".

Ullmanns Encyl. Of Ind. Chem. (month unavailable) 1991, vol. A 17, pp. 411–455, G. Booth, Thorpe House, "Nitro Compounds, Aromatic".

Ency. of Chem. Tech. (month unavailable), 1981, vol. 15, pp. 841–853, Kirk–Othmer "Nitration".

G. A. Olah et al, "Nitration Methods and Mechanisms" (month unavailable) 1989, pp. 1, 2, 13, 14.

J. Org Chem, 1982, 47, pp. 596–598.*

* cited by examiner

Primary Examiner—Samuel Barts
(74) Attorney, Agent, or Firm—Joseph C. Gil; Lyndanne M. Whalen

(57) ABSTRACT

A process for producing a mixture of isomers of dinitronaphthalene by nitration of nitronaphthalene, in which nitronaphthalene, optionally in an inert organic solvent, is reacted with 1 to 20 times the equivalent quantity, based on the quantity of nitronaphthalene, of 50% to 100% nitric acid in the presence of a solid, perfluorinated, strongly acidic ion exchanger.

7 Claims, No Drawings

METHOD FOR PRODUCING A DINITRONAPHTHALENE-ISOMER MIXTURE HAVING A HIGH 1,5-DINITRONAPHTHALENE PROPORTION

This invention relates to the production of a mixture of isomers of dinitronaphthalene containing an increased proportion of 1,5-dinitronaphthalene (referred to below as 1,5-DNN) by the nitration of pure 1-nitronaphthalene or of a crude nitronaphthalene mixture. 1,5-Dinitronaphthalene is a key compound for the production of 1,5-diaminonaphthalene (referred to below as 1,5-NDA). This is, inter alia, the starting compound for the production of 1,5-diisocyanatonaphthalene (1,5-NDI, trade name Desmodur 15®). 1,5-NDI is used as the isocyanate component in polyurethanes.

The production of nitrated aromatics has been known for a long time (G. A. Olah et al., Nitration: Methods and Mechanisms, VCH, New York, 1989). For decades, corresponding nitroaromatics have been produced industrially by nitration using a mixture of sulfuric acid and nitric acid (so-called mixed acid or nitrating acid). Nowadays polynitrations, for example dinitrations, are mostly carried out on the large scale by a two-step nitration (Kirk-Othmer, Encyclopedia of Chemical Technology, 1981, Vol. 15 and Ullmann, Encyclopedia of Industrial Chemistry, 1991, Vol. A17, pages 411–455).

The nitration of naphthalene (Houben-Weyl, Methoden der Organischen Chemie, 1971, Vol. 10, pages 492–495) yields a mixture of the isomers 1-nitronaphthalene and 2-nitronaphthalene in the ratio of about 95:5. In the nitration of the isomerically pure 1-nitronaphthalene using a mixture of sulfuric acid and nitric acid, a mixture of 1,5- and 1,8-dinitronaphthalene in the ratio of about 1:2 is formed, in addition to about 5% of other isomers (for example, 1,6- and 1,7-DNN). The unfavourable selectivity of the reaction leads in the production of 1,5-DNN chiefly to a high and undesirable content of 1,8-DNN.

DE-A 11 50 965 reports the increase in the selectivity by a rapid and intensive mixing of 1-nitronaphthalene dissolved in sulfuric acid together with nitrating acid. A disadvantage of this process is the considerable quantity of sulfuric acid used as solvent, the working-up of which is very expensive and cost-intensive. In addition, considerable quantities of trinitrated products, which both significantly decrease the yield of 1,5-DNN and are to be considered critical as regards safety regulations, can be formed in this process—particularly in the adiabatic reaction procedure described in the above-mentioned prior art.

WO 94/19310 describes nitrations of nitroaromatics on aluminium silicates partially doped with heavy metal, so-called claycops, as solid catalyst, which deliver high yields of dinitrated products together with small quantities of trinitroaromatics. However, nitrations of 1-nitronaphthalene carried out by this process yield ratios of isomers similar to those in classical nitrations with mixed acid.

Nitrations with nitric acid in organic solvents, for example, dichloroethane, and azeotropic removal of the water of the reaction are described in DE-A 24 53 529. They deliver dinitronaphthalene in high yields, but without influencing the ratio of isomers.

The object, accordingly, was to find a process for producing a mixture of isomers of dinitronaphthalene containing a high proportion of 1,5-dinitronaphthalene by nitration of 1-nitronaphthalene, in which mixed or nitrating acid, which simply entails expensive working up, need not be used.

Surprisingly, it has now been found that a shift of the ratio of isomers towards 1,5-DNN is possible where solid, perfluorinated, strongly acidic ion exchangers are used as catalyst in the nitration of 1-nitronaphthalene. The reaction is carried out in an excess of nitric acid, which can be recovered on completion of the reaction and after concentration.

The invention therefore provides a process for producing a mixture of isomers of dinitronaphthalene by nitration of nitronaphthalene, wherein nitronaphthalene, optionally in an inert organic solvent, is reacted with 1 to 20 times the equivalent quantity, based on nitronaphthalene, of 50% to 100% nitric acid in the presence of a solid, perfluorinated, strongly acidic ion exchanger. 1 to 20 times the equivalent quantity corresponds, in the case e.g. of a 65% nitric acid, to 33 wt. % to 92 wt. %, based on the solution, and in the case of an 100% nitric acid, to 26 wt. % to 88 wt. %.

The mixtures of DNN isomers produced according to the invention contain a surprisingly high proportion of the 1,5-DNN isomer. Conventionally, the content of 1,5-DNN is more than 30 wt. %, in particular between 34 and 50 wt. %. The content of other secondary products, in particular of other isomers of dinitronaphthalene and of more highly nitrated products, is smaller than in comparable nitrations with mixed acid.

The starting product used can be pure 1-nitronaphthalene or even a crude nitronaphthalene mixture, such as is obtained as crude product in the nitration of naphthalene.

The solid, perfluorinated, strongly acidic ion exchanger catalyses the reaction to form the 1,5-dinitronaphthalene-enriched end product. Such perfluorinated, strongly acidic ion exchangers are known in prior art and are commercially available, for example, under the trade name Nafion®. Preferably an ion-exchange resin with the trade name Nafion® NR 50 Superacid Catalyst (Dupont) is used.

The ion exchanger used as catalyst is chemically inert and can be easily removed from the reaction batch, for example, by filtration. A working up, as in the case of the diluted and organically contaminated sulfuric acid which accumulates during nitrations with mixed acid (nitric acid/sulfuric acid mixture), is advantageously omitted in the process according to the invention.

The concentration of the nitric acid is between 50% and 100%, preferably between 60% and 80%. The quantity of nitric acid added is between 1 equivalent and 20 equivalents, based on the quantity of nitronaphthalene used. In the case of a 65% nitric acid, this corresponds to 33 to 92 wt. %. Preferably quantities of nitric acid of between 3 equivalents (in the case of 65% nitric acid: 62.7 wt. %) and 12 equivalents (corresponding to 87.0 wt. % of 65% nitric acid) are used.

The process is conventionally carried out at temperatures of between 20° C. and 100° C., preferably 80° C.

To ensure a complete reaction, the conversion is carried out with thorough mixing of the reaction mixture, for example, by intensive stirring for a reaction period of between 20 minutes and 8 hours, for example, 3 hours.

In the absence of additional solvent, the process according to the invention can only be carried out in an excess of nitric acid, or else optionally after the introduction of a solvent.

In this connection, the 1,5-selectivity can, surprisingly, be increased even further in the presence of an inert organic solvent.

The process according to the invention is therefore preferably carried out in the presence of an inert organic solvent. Suitable solvents of this kind are polar compounds which are inert in the reaction medium. Examples of such solvents are sulfolane or nitroalkanes, such as, for example, nitromethane.

The process according to the invention is preferably carried out in the presence of sulfolane as organic solvent.

Unreacted nitronaphthalene, excess nitric acid and solvent can be returned to the process.

The quantity of organic solvent added is between 0.1 and 20 parts and preferably between 0.5 and 3 parts, based on the quantity of nitronaphthalene used. The concentration of the nitric acid is adjusted according to the quantity of solvent added and is between 50% and 100%, preferably 60% to 80%.

The mixture of isomers of dinitronaphthalene can be separated into the isomeric dinitronaphthalenes in known manner, for example, by fractional crystallisation. Such separations of isomers, for example, with dimethylformamide or dichloroethane as solvent, have already been described (cf. Houben-Weyl, Methoden der organischen Chemie, 1971, Vol. 10, page 494).

The invention also provides mixtures of isomers consisting of 1,5- and 1,8-dinitronaphthalene, having a 1,5-dinitronaphthalene content of more than 30 wt. %, in particular of between 34 and 50 wt. %.

These mixtures of isomers of dinitronaphthalene are preferably obtained by the process according to the invention described above.

The 1,5-DNN can be separated from the mixture of isomers according to the invention in known manner and used for the production of 1,5-NDA and 1,5-NDI. The following Examples are intended to explain the invention, without thereby limiting its scope.

EXAMPLES

Pure 1-nitronaphthalene was used as the starting material.

The ion exchanger used as catalyst, with the trade name Nafion® NR 50 Superacid Catalyst (Dupont), in the Examples below is referred to simply as Nafion.

1. Nitration of 1-nitronaphthalene Using Nitric Acid with Nafion as Catalyst 1.1 Nitration with Nafion-H and 0.6 mol Nitric Acid 10 g Nafion and 17.3 g (0.1 mol) 1-nitronaphthalene were added to 58.2 g of 65% (w/w) nitric acid (corresponding to 0.6 mol). The batch was then stirred for 3 hours at 80° C. Working up was carried out by introducing the reaction batch into 1000 ml ice water, filtering off and subsequently drying the solid substance. The dinitronaphthalene was separated from the catalyst by extraction with dioxane. Here the solid substance was placed in 200 ml dioxane at 90° C. and stirred for 30 minutes, then the catalyst was filtered off and the dioxane was removed by distillation.

The isomeric composition of the residue was determined by gas chromatography (HP 5890, column: 25 m SE 30, injector: 300° C., detector (FID): 320° C., temperature programme: Start: 100° C., heating rate: 10° C./min, end temperature: 320° C., quantity of sample: 2% in dioxane, quantity injected: 1 µl).

1.2 Nitration with Nafion-H and 8 mol Nitric Acid 10 g Nafion and 17.3 g (0.1 mol) 1-nitronaphthalene were added to 77.6 g of 65% (w/w) nitric acid (corresponding to 0.8 mol). The batch was then stirred for 3 hours at 80° C. The working up and determination of the isomeric composition were carried out as in 1.1.

1.3 Nitration without Nafion-H and 6 mol Nitric Acid (Comparison Example)

17.3 g (0.1 mol) 1-nitronaphthalene was added to 58.2 g of 65% (w/w) nitric acid (corresponding to 0.6 mol). No Nafion was added. The batch was then stirred for 3 hours at 80° C. Working up was carried out by introducing the reaction batch into 1000 ml ice water and filtering off the solid substance. The determination of the isomeric composition was carried out as in 1.1.

1.4 Nitration with $H_2SO_4$ and 6 mol Nitric Acid (Comparison Example)

17.3 g (0.1 mol) 1-nitronaphthalene was added to 58.2 g of 65% (w/w) nitric acid (corresponding to 0.6 mol) and 10.0 g sulfuric acid (0.1 mol). The batch was then stirred for 3 hours at 80° C. Working up was carried out by introducing the reaction batch into 1000 ml ice water and filtering off the solid substance. The determination of the isomeric composition was carried out as in 1.1.

The experimentally determined isomeric compositions are given in Table 1. In nitrations with Nafion, there is a higher 1,5-yield and an improved ratio of (1.5)/(1.8)-DNN. This is in accordance with a corresponding increase in the 1,5-selectivity in the nitration.

TABLE 1

Composition of the product mixture in the nitration of 1-nitronaphthalene with nitric acid (Examples 1.1 to 1.4); the equivalents of the nitrating agent, the concentration of the nitric acid used and the reaction temperature are shown. The composition of the product mixture (in per cent) was determined by gas chromatography. The proportion of 1-nitronaphthalene (1-MNN), 1,5-dinitronaphthalene (1,5-DNN), 1,8-dinitronaphthalene (1,8-DNN) and the sum of the proportions of other DNN-isomers and trinitronaphthalene (DNN + TNN) are shown, as well as the ratio of the products 1,5-DNN and 1,8-DNN $\left(\frac{1,5-DNN}{1,8-DNN}\right)$ formed.

| Ex. | $HNO_3$ | Catalyst solvent | 1-MNN | 1,5-DNN | 1,8-DNN | $\frac{1,5-DNN}{1,8-DNN}$ | Σ of other DNN & TNN |
|---|---|---|---|---|---|---|---|
| 1.1 | 6 × 65%, 80° C. | Naflon | 22.1 | 34.1 | 38.0 | 0.90 | 5.8 |

TABLE 1-continued

Composition of the product mixture in the nitration of 1-nitronaphthalene with nitric acid (Examples 1.1 to 1.4); the equivalents of the nitrating agent, the concentration of the nitric acid used and the reaction temperature are shown. The composition of the product mixture (in per cent) was determined by gas chromatography. The proportion of 1-nitronaphthalene (1-MNN), 1,5-dinitronaphthalene (1,5-DNN), 1,8-dinitronaphthalene (1,8-DNN) and the sum of the proportions of other DNN-isomers and trinitronaphthalene (DNN + TNN) are shown, as well as the ratio of the products 1,5-DNN and 1,8-DNN $\left(\frac{1,5-DNN}{1,8-DNN}\right)$ formed.

| Ex. | HNO$_3$ | Catalyst solvent | 1-MNN | 1,5-DNN | 1,8-DNN | $\frac{1,5-DNN}{1,8-DNN}$ | Σ of other DNN & TNN |
|---|---|---|---|---|---|---|---|
| 1.2 | 6 × 65%, 80° C. | Naflon | 2.7 | 43.5 | 49.3 | 0.88 | 4.5 |
| 1.3 | 8 × 65%, 80° C. | — | 33.8 | 22.5 | 36.3 | 0.62 | 7.4 |
| 1.4 | 6 × 65%, 80° C. | H$_2$SO$_4$ | 0.1 | 29.6 | 57.3 | 0.52 | 13.0 |

2. Nitration of 1-nitronaphthalene Using Nitric Acid with Nafion as Catalyst in the Presence of an Organic Solvent 2.1 Nitration with Nafion-H and 0.6 mol Nitric Acid in the Presence of Sulfolane 10 g Nafion, 30 g sulfolane and 17.3 g (0.1 mol) 1-nitronaphthalene were added to 58.2 g of 65% (w/w) nitric acid (corresponding to 0.6 mol). The batch was then stirred for 3 hours at 100° C. The working up and determination of the isomeric composition were carried out as in 1.1.

2.2 Nitration with Nafion-H and 0.6 mol Nitric Acid in the Presence of Nitromethane 10 g Nafion, 30 g nitromethane and 17.3 g (0.1 mol) 1-nitronaphthalene were added to 58.2 g of 65% (w/w) nitric acid (corresponding to 0.6 mol). The batch was then stirred for 3 hours at 100° C. The working up and determination of the isomeric composition were carried out as in 1.1.

The experimentally determined isomeric compositions are given in Table 2. The addition of the solvent results in higher ratios of (1.5)/(1.8)-DNN. This is in accordance with a corresponding increase in the 1,5-selectivity in the nitration.

TABLE 2

Composition of the product mixture in the nitration of 1-nitronaphthalene with nitric acid and addition of a solvent (Examples 2.1 to 2.2); the equivalents of the nitrating agent, the concentration of the nitric acid used and the reaction temperature are shown. The composition of the product mixture (in per cent) was determined by gas chromatography.

| Ex. | HNO$_3$ | Catalyst/ solvent | 1-MNN | 1,5-DNN | 1,8-DNN | $\frac{1,5-DNN}{1,8-DNN}$ | Σ of other DNN & TNN |
|---|---|---|---|---|---|---|---|
| 2.1 | 6 × 65%, 100° C. | Naflon/ sulfolane | 68.9 | 15.0 | 9.1 | 1.65 | 7.0 |
| 2.2 | 8 × 65%, 100° C. | Naflon/ nitro-methane | 55.6 | 18.7 | 17.9 | 1.04 | 7.8 |

What is claimed is:

1. A process for the production of an isomeric mixture of dinitronaphthalene comprising reacting a) nitronaphthalene with b) nitric acid having a concentration of from 50 to 100% in an amount that is from 1 to 20 times the equivalent amount of a) in the presence of c) a solid, perfluorinated, strongly acidic ion exchanger.

2. The process of claim 1 in which an inert organic solvent is present in a).

3. The process of claim 1 in which a) is a crude nitronaphthalene mixture.

4. The process of claim 2 in which the inert organic solvent is a nitroalkane and/or a sulfolane.

5. The process of claim 4 in which the inert organic solvent is used in an amount of from 0.1 to about 20 parts by weight, based on the weight a).

6. An isomeric mixture of dinitronaphthalene in which from about 45 to about 60% by weight is 1,8-dinitronaphthalene and from about 35 to about 50% by weight is 1,5-dinitronaphthalene and in which the ratio of 1,5-dinitronaphthalene to 1,8-dinitronaphthalene is at least 0.88.

7. The isomeric mixture of claim 6 which has been produced by reacting a) nitronaphthalene with b) nitric acid having a concentration of from 50 to 100% and an amount of from 1 to 20 times the equivalent amount of a) in the presence of c) a solid, perfluorinated, strongly acidic ion exchanger.

* * * * *